US00PP15148P2

(12) United States Plant Patent
Oudolf

(10) Patent No.: US PP15,148 P2
(45) Date of Patent: Sep. 14, 2004

(54) SALVIA PLANT NAMED 'RHAPSODY IN BLUE'

(50) Latin Name: *Salvia hybrida*
Varietal Denomination: Rhapsody in Blue

(75) Inventor: Petrus Hendricus Oudolf, Hummelo (NL)

(73) Assignee: Future Plants Licentie BV, Lisserbroek (NL)

( * ) Notice: Subject to any disclaimer, the term of this patent is extended or adjusted under 35 U.S.C. 154(b) by 0 days.

(21) Appl. No.: 10/437,936

(22) Filed: May 13, 2003

(51) Int. Cl.[7] ..... A01H 5/00
(52) U.S. Cl. ..... Plt./263
(58) Field of Search ..... Plt./226, 263

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of Salvia plant named 'Rhapsody in Blue', characterized by its upright and relatively compact plant habit; very freely basal branching habit; dense and bushy plant form; freely flowering habit; and blue violet-colored flowers.

1 Drawing Sheet

Botanical classification/cultivar designation: Salvia hybrida cultivar Rhapsody in Blue.

BACKGROUND OF THE INVENTION

The present Invention relates to a new and distinct cultivar of Salvia plant, botanically known as Salvia hybrida, and hereinafter referred to by the name 'Rhapsody in Blue'.

The new Salvia is a product of a planned breeding program conducted by the Inventor in Hummelo, The Netherlands. The objective of the breeding program was to create new compact Salvia cultivars with numerous flowers with attractive coloration.

The new Salvia originated from a self-pollination made by the Inventor during the summer of 1999 of the Salvia hybrida cultivar Amathyst, not patented. The new Salvia was discovered and selected by the Inventor during the spring of 2000 as a single flowering plant within the progeny of the stated self-pollination grown in a controlled environment in Hummelo, The Netherlands.

Asexual reproduction of the new cultivar by cuttings and divisions taken at Hummelo, The Netherlands, since the summer of 2000, has shown that the unique features of this new Salvia are stable and reproduced true to type in successive generations.

SUMMARY OF THE INVENTION

Plants of the cultivar Rhapsody in Blue have not been observed under all possible environmental conditions. The phenotype may vary somewhat with variations in environment such as temperature and light intensity without, however, any variance in genotype.

The following traits have been repeatedly observed and are determined to be the unique characteristics of 'Rhapsody in Blue'. These characteristics in combination distinguish 'Rhapsody in Blue' as a new and distinct Salvia cultivar:

1. Upright and relatively compact plant habit.
2. Very freely basal branching, dense and bushy plant form.
3. Freely flowering habit.
4. Blue violet-colored flowers.

Plants of the new Salvia are more compact than plants of the cultivar Amathyst.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new Salvia. The photograph comprises a side perspective view of a typical flowering plant of 'Rhapsody in Blue' grown in a outdoor nursery.

DETAILED BOTANICAL DESCRIPTION

Plants shown in the aforementioned photograph and used in the following description were grown under conditions which closely approximate commercial production conditions during the late spring in an outdoor nursery in Lisserbroek, The Netherlands. During the production of the plants, day temperatures ranged from 14 to 25° C. and night temperatures ranged from 4 to 16° C. Plants in the photograph and used for the description were about one year old when the photograph and description were taken. In the following description, color references are made to The Royal Horticultural Society Colour Chart, 2001 Edition, except where general terms of ordinary dictionary significance are used.

Botanical classification: Salvia hybrida cultivar Rhapsody in Blue.

Parentage: Self-pollination of the Salvia hybrida cultivar Amathyst, not patented.

Propagation:

*Type.*—By cuttings.

*Time to produce a rooted young plant.*—About 60 days at 16 to 22° C.

*Root description.*—Thick.

Plant description:

*Form.*—Perennial. Upright and relatively compact plant habit; broad inverted triangle. Very freely basal branching with about 37 flowering stems per plant;

dense and bushy plant habit; moderately vigorous growth habit. Numerous flowers arranged in verticillasters on crowded spikes.

*Plant height.*—About 62 cm.

*Plant width.*—About 62 cm.

*Flowering stem description.*—Length: About 52 cm. Diameter: About 5 mm. Internode length: About 12 cm. Strength: Strong. Texture: Densely pubescence. Color: 143A.

*Foliage description.*—Arrangement: Opposite, simple. Length: About 12.5 cm. Width: About 5.6 cm. Shape: Ovate, elongated. Apex: Acute. Base: Cordate. Margin: Crenate. Texture, upper and lower surfaces: Fine pubescence; rugose. Venation pattern: Pinnate. Fragrance: When rubbed, sage-like. Color: Developing and fully expanded foliage, upper surface: 137A. Developing and fully expanded foliage, lower surface: 137B. Venation, upper surface: 144B to 144C. Venation, lower surface: 144B. Petiole length: About 3.8 cm. Petiole diameter: About 3 mm. Petiole color: 144B.

Flower description:

*Flower arrangement and shape.*—Single labiate flowers in verticillasters on spikes; flowers face outwardly. Freely flowering, flowers in whorls of six; about 78 flowers per spike.

*Natural flowering season.*—Continuous from mid-May into July in The Netherlands.

*Flower longevity on the plant.*—Individual flowers last about five days on the plant. Flowers not persistent.

*Flower buds.*—Length: About 9 mm. Diameter: About 5 mm. Shape: Ovoid. Color: 93A.

*Inflorescence size.*—Length: About 18 cm. Diameter: About 4.4 cm.

*Flowers.*—Diameter: About 1.6 cm by 7 mm. Depth (height): About 2.4 cm.

*Petals.*—Arrangement: Labiate; one upper lip and one lower lip with three lobes; lips fused at the base. Length: Upper petal: About 1.9 cm. Lower petal: About 1.7 cm. Width: Upper petal: About 1 mm. Lower petal: About 7 mm. Shape: Upper petal: Broadly elliptic. Lower petal: Spatulate. Apex: Upper petal: Emarginate. Lower petal: Rounded. Margin, upper and lower petals: Entire. Texture, upper and lower petals: Pubescent. Color: Upper petal: When opening and fully opened, upper surface: 93C. When opening and fully opened, lower surface: 93A. Lower petal: When opening and fully opened, upper surface: 93B with central spot, 86A. When opening and fully opened, lower surface: 93B with central spot, 86A.

*Sepals.*—Arrangement: Five sepals fused into a tube. Length: About 9 mm. Width: About 2 mm. Shape: Elliptic. Apex: Acute. Margin: Entire. Texture, upper and lower surfaces: Pubescent. Color: When opening, upper surface: 146A. When opening, lower surface: 187A. Fully opened, upper surface: 143C with longitudinal stripes, 143A. Fully opened, lower surface: 138A.

*Flower bracts.*—Quantity per verticillaster: Two. Length: About 1.3 cm. Width: About 7 mm. Shape: Deltoid. Apex: Apiculate. Texture, upper and lower surfaces: Pubescent. Color, upper and lower surfaces: 144A to 144B.

*Peduncles.*—Strength: Strong. Length: About 62 cm. Diameter: About 2.5 cm. Aspect: Mostly upright. Color: 143A; towards the apex, N187A.

*Pedicels.*—Strength: Strong. Length: About 2 mm. Diameter: About 0.5 mm. Aspect: About 45° from vertical. Color: 138A.

*Reproductive organs.*—Stamens: Quantity per flower: Two. Anther shape: Narrowly elliptic. Anther length: About 2 mm. Anther color: 183A. Filament length: About 1.3 cm. Filament color: N88D. Pollen amount: None observed. Pistils: Quantity per flower: One. Pistil length: About 2.2 cm. Stigma shape: Two-parted, cleft. Stigma color: 93A. Style length: About 2 cm. Style color: 92D. Ovary color: N144A.

*Seed/fruit.*—Seed and fruit production has not been observed.

Disease/pest resistance: Plants of the new Salvia have not been noted to be resistant to pathogens and pests common to Salvia.

Weather tolerance: Plants of the new Salvia have exhibited good tolerance to rain and wind and have been observed to tolerate temperatures from −25 to 35° C.

It is claimed:

1. A new and distinct cultivar of Salvia plant named 'Rhapsody in Blue', as illustrated and described.

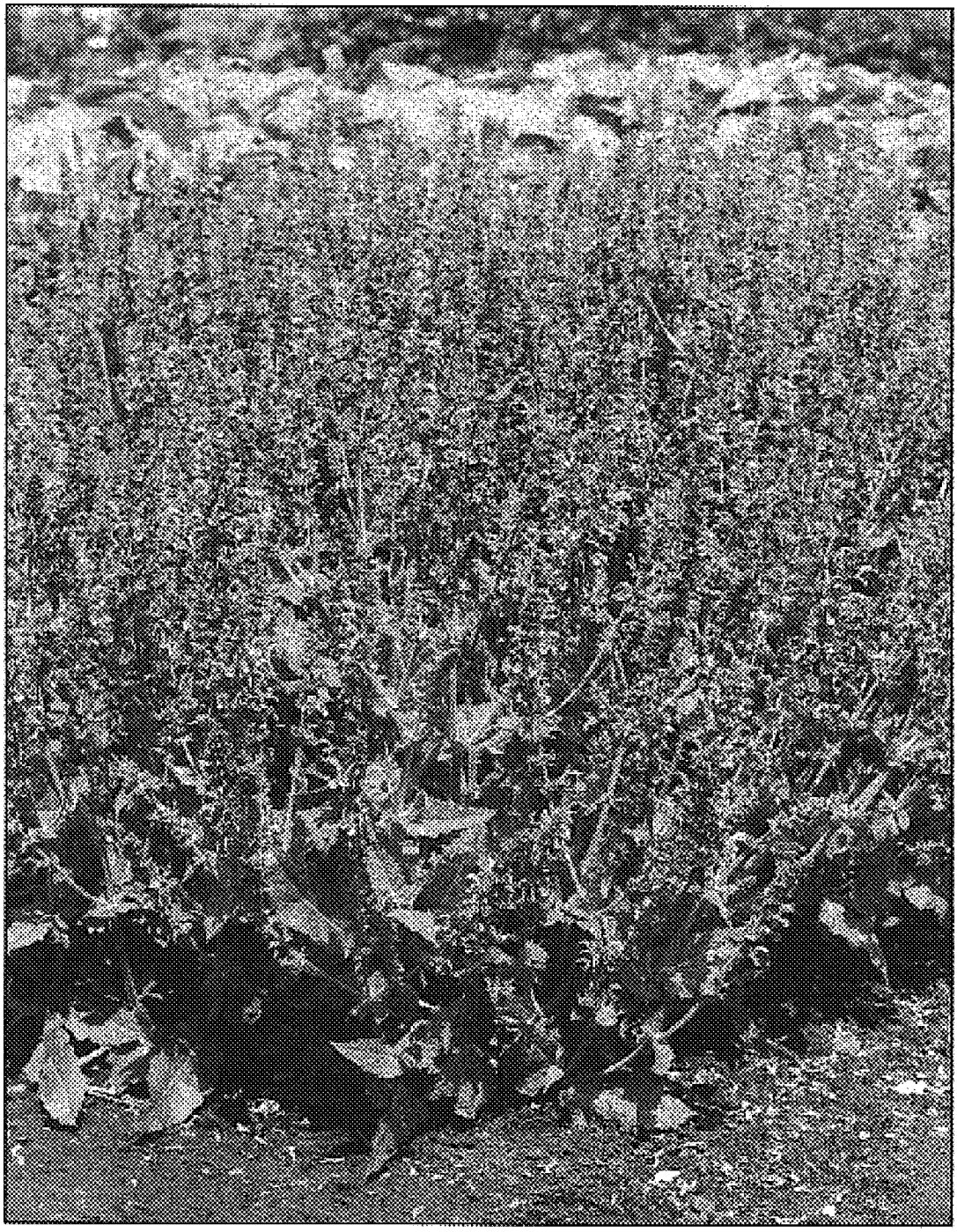

* * * * *